United States Patent [19]

Takashima et al.

[11] Patent Number: 4,794,106

[45] Date of Patent: Dec. 27, 1988

[54] CREAM

[75] Inventors: Yasuji Takashima; Shigeo Tanaka; Kenji Tsunoda; Ichirou Kawamata, all of Saitama; Hiroshi Murayama, Tokyo, all of Japan

[73] Assignee: Taisho Pharmaceutical Co., Ltd., Tokyo, Japan

[21] Appl. No.: 902,002

[22] Filed: Aug. 28, 1986

Related U.S. Application Data

[63] Continuation of Ser. No. 574,020, Jan. 26, 1984, abandoned.

[30] Foreign Application Priority Data

Jan. 31, 1983 [JP] Japan ................... 58-14302

[51] Int. Cl.$^4$ ............... A61K 31/56; A61K 31/58; C07J 5/00
[52] U.S. Cl. ...................... 514/179; 514/26; 514/943; 514/969
[58] Field of Search ............. 514/943, 179, 26, 969

[56] References Cited

U.S. PATENT DOCUMENTS

| | | | |
|---|---|---|---|
| 4,211,769 | 7/1980 | Okada et al. | 514/800 |
| 4,289,764 | 9/1981 | Yarrow et al. | 424/243 |
| 4,290,962 | 9/1981 | Tachi et al. | 260/397.45 |
| 4,294,852 | 10/1981 | Wildnawer et al. | 424/240 |
| 4,305,936 | 12/1981 | Klein | 424/243 |
| 4,434,179 | 2/1984 | Kobayashi et al. | 514/738 |
| 4,473,565 | 9/1984 | Rovee et al. | 514/179 |
| 4,619,926 | 10/1986 | Eckert | 514/375 |
| 4,637,930 | 1/1987 | Konno et al. | 514/947 |
| 4,654,209 | 3/1987 | Leslie et al. | 514/179 |

OTHER PUBLICATIONS

McCutcheon's Detergents and Emulsifiers 1982, pp. 120–121.

*Primary Examiner*—Ronald W. Griffin
*Assistant Examiner*—Nancy S. Carson
*Attorney, Agent, or Firm*—Wenderoth, Lind & Ponack

[57] ABSTRACT

An oil-in-water type cream comprising
- (a) 0.01 to 0.5% by weight of hydrocortisone butyrate proponate,
- (b) 5 to 50% by weight of a higher paraffinic hydrocarbon,
- (c) 3 to 15% by weight of a surface-active agent,
- (d) 30 to 65% by weight of purified water,
- (e) not more than 20% by weight of a monohydric higher alcohol,
- (f) not more than 20% by weight of a dihdyric or trihydric alcohol, and
- (g) a pharmaceutically acceptable acid in an amount required to adjust the pH of the cream to a value in the range of 3.5 to 6.5 when it is diluted with water to 20 times its volume.

9 Claims, No Drawings

CREAM

This application is a continuation of now abandoned application Ser. No. 574,020, filed Jan. 26, 1984.

This invention relates to a cream, and more specifically to an oil-in-water type cream comprising hydrocortisone butyrate propionate having excellent anti-inflammatory activity as a main active ingredient.

Hydrocortisone butyrate propionate is also known as 17α-butyryloxy-21-propionyloxy-11β-hydroxy-4-pregnene-3,20-dione, and is a known corticosteroidal compound having excellent anti-inflammatory activity which is topically administrable with little side-effects (see, for example, U.S. Pat. No. 4,290,962).

The present inventors attempted to formulate hydrocortisone butyrate propionate into a pharmaceutical composition in accordance with an ordinary recipe of oil-in-water type creams. Oil-in-water type creams having incorporated therein isopropyl myristate or a fatty acid triglyceride have been used in practical applications because of their good feel during use or good solubility of the active ingredient. In Pharm. J., 184, 509 (1960), Hadgraft et al. reported a base of the following formulation for these creams.

| | |
|---|---|
| Isopropyl myristate | 24 parts by weight |
| Purified lanolin | 16 parts by weight |
| Emulsified wax | 5 parts by weight |
| Purified water to make | 100 parts by weight |

A cream obtained by mixing hydrocortisone butyrate propionate with this cream base, however, has been found to have poor absorbability from the skin and poor storage stability.

The present inventors made extensive investigations in order to remove this defect. These investigations have led to the discovery that a cream containing hydrocortisone butyrate propionate and having excellent skin absorbability and storage stability can be obtained by dispersing hydrocortisone butyrate propionate in a cream base composed of a higher paraffinic hydrocarbon, water and a surface-active agent and adjusting the pH of the cream such that when diluted with distilled water to 20 times its volume, it has a pH in the range of 3.5 to 6.5.

According to this invention, there is provided an oil-in-water type cream comprising
(a) 0.01 to 0.5% by weight of hydrocortisone butyrate propionate,
(b) 5 to 50% by weight of a higher paraffinic hydrocarbon,
(c) 3 to 15% by weight of a surface-active agent,
(d) 30 to 65% by weight of purified water,
(e) not more than 20% by weight of a monohydric higher alcohol,
(f) not more than 20% by weight of a dihydric or trihydric alcohol, and
(g) a pharmaceutically acceptable acid in an amount required to adjust the pH of the cream to a value in the range of 3.5 to 6.5 when it is diluted with water to 20 times its volume.

It should be understood that in the present specification and the appended claims, all percentages showing the concentrations of the ingredients of the cream are based on the weight of the cream.

The ingredients of the cream of this invention and a method for its preparation will now be described in detail.

The higher paraffinic hydrocarbon used in the cream of this invention includes any pharmaceutically acceptable higher paraffinic hydrocarbons which are generally used in the preparation of oil-in-water type creams. Generally, it may be one, or a mixture, of straight or branched saturated aliphatic hydrocarbons having 16 to 40 carbon atoms. Specific examples of such a higher paraffinic hydrocarbon include light liquid paraffin, liquid paraffin, white Vaseline (petrolatum), yellow Vaseline, paraffin, and ceresin. The higher paraffinic hydrocarbon should have a viscosity suitable for skin coatability of the resulting cream. Desirably, it has a viscosity of generally about 10 to $10^6$, preferably $10^3$ to about $10^5$, centipoises at 20° C. Accordingly, when the above-exemplified higher paraffinic hydrocarbons, if used singly, cannot provide viscosities in the above-mentioned range, the viscosity is desirably adjusted by using two or more of the higher paraffinic hydrocarbons in combination. White Vaseline and liquid paraffin are especially preferred higher paraffinic hydrocarbons.

The higher paraffinic hydrocarbon is used in a concentration of 5 to 50% by weight, preferably 15 to 40% by weight, more preferably 20 to 30% by weight.

The surface-active agent serves to maintain the cream of this invention in an oil-in-water type, and any surface-active agents frequently used in the preparation of oil-in-water pharmaceutical preparations can be used. Suitable surfactants include nonionic surfactants such as sorbitan fatty acid esters (e.g. polyoxyethylene sorbitan fatty acid esters), sorbitan, glycerin fatty acid esters and propylene glycol fatty acid esters. More specifically, those sold under the tradenames Nikkol T010, TS10, SS10, S010, MGS, and MYS25 by Nikko Chemicals Co., Ltd., Japan may be advantageously used. These surfactants may be used singly or in combination. In some cases, it is possible to use a combination of such a nonionic surfactant with a cationic or anionic surfactant such as an alkylsulfuric acid salt (e.g., sodium laurylsulfate). In any case, the one or more surfactants used should preferably have a total HLB of 7 to 16, especially 9 to 12. A mixture of polyoxyethylene sorbitan monostearate and sorbitan monostearate can be used especially preferably in this invention.

The surface-active agent can be present in the cream of this invention in a concentration of 3 to 15% by weight, preferably 4 to 10% by weight, depending upon the kind of surface active agent.

Purified water as a major ingredient of the cream of this invention denotes water obtained by distilling ordinary water (tap water or well water) or purifying it through an ion-exchange resin. It accounts for 30 to 65% by weight, preferably 40 to 55% by weight, more preferably 45 to 50% by weight, of the cream.

As required, and preferably, a monohydric higher alcohol may be included in the cream of this invention in order to improve its appearance or properties. The monohydric higher alcohol may include straight or branched saturated aliphatic alcohols having 12 to 32 carbon atoms, preferably 14 to 20 carbon atoms, specifically cetyl alcohol, stearyl alcohol, cetostearyl alcohol, myristyl alcohol, etc. These alcohols may be used singly or in combination.

The monohydric higher alcohol may be included in a concentration of not more than 20% by weight, preferably 5 to 15% by weight, more preferably 7 to 10% by weight.

As required, and preferably, a dihydric or trihydric alcohol may be included in the cream of this invention in order to improve its feel during use and inhibit vaporization of water during application. The dihydric alcohol includes, for example, glycols having 2 to 6 carbon atoms, particularly 2 to 4 carbon atoms, such as ethylene glycol, propylene glycol and 1,3-butanediol. Glycerol is preferred as the trihydric alcohol. In particular, the glycols are good solvents for hydrocortisone butyrate propionate, and use of these glycols improves the operability of preparing the cream and increases the skin absorbability of hydrocortisone butyrate propionate.

The dihydric or trihydric alcohols may be used singly or in combination. The amount of the dihydric or trihydric alcohol is not more than 20% by weight, preferably 5 to 15% by weight, more preferably 7 to 12% by weight.

One great characteristic of the cream of this invention is that the pH of the cream is adjusted by using a pharmaceutically acceptable acid so that when diluted with distilled water to 20 times its volume, the cream has a pH in the range of 3.5 to 6.5, preferably 4.0 to 6.0, more preferably 4.5 to 5.5. This markedly increases the storage stability of hydrocortisone butyrate propionate as the main active ingredient in the cream. Examples of the acid used for pH adjustment include comparatively weakly acidic organic or inorganic acids such as citric acid, lactic acid, phosphoric acid, tartaric acid, malic acid and maleic acid.

In addition to the above ingredients, the cream of this invention may further contain other pharmacologically effective substances in specified concentrations, for example 0.1 to 0.5% by weight of gentamicin sulfate, 0.1 to 0.5% by weight of fradiomycin sulfate, 0.1 to 1% by weight of tetracycline and 5 to 10% by weight of crotamiton (crotonyl-N-ethyl-o-toluidine).

As required, the cream of this invention may further contain 0.1 to 0.3% by weight of an antiseptic (for example, alkyl p-hydroxybenzoates such as methyl paraben, ethyl paraben and propyl paraben), 1 to 10% by weight of a moisture-retaining agent such as urea, sodium lactate and pyrrolidonecarboxylic acid), a perfume, etc.

The concentration of hydrocortisone butyrate propionate as the active ingredient of the cream of this invention can be varied within the range of 0.01 to 0.5% by weight, preferably within the range of 0.025 to 0.2% by weight.

The cream of this invention can be prepared by methods known per se. For example, when the dihydric or trihydric alcohol is not used, it can be formulated by adding hydrocortisone butyrate propionate and oil-soluble ingredients (such as the monohydric higher alcohol, and the alkyl p-hydroxybenzoate) to a mixture of the higher paraffinic hydrocarbon and the surface-active agent, fully mixing them at a temperature of about 50° to about 80° C. to form a component A, separately dissolving the pH adjusting agent (acid) in purified water at a temperature of about 50° to about 80° C. to form a component B, then adding the component B in small portions to the component A with stirring at about 50° to about 80° C. to form an emulsion, and cooling the emulsion with stirring.

In view of the operability of preparation, the dihydric or trihydric alcohol is preferably used. In this case, the cream of the invention is prepared, for example, by adding the aforesaid oil-soluble ingredients to a mixture of the higher paraffinic hydrocarbon and the surface-active agent, dissolving them at a temperature of about 50° to about 80° C. to form a component A′, separately dissolving hydrocortisone butyrate propionate in the dihydric or trihydric alcohol at about 50° to about 80° C. to form a component B′ and dissolving the pH adjusting agent in purified water at the aforesaid temperature to form a component C′, then adding the component B′ in small portions to the component A′ with stirring at about 50° to about 80° C., after the addition further adding the component C′ to form an emulsion, and cooling the emulsion with stirring.

Since the cream of this invention has excellent skin absorbability of hydrocortisone butyrate propionate and excellent storage stability, it is very effective in the curing and treatment of diseases involving inflammation such as acute eczema, chronic eczema, seborrheic eczema, atopic dermatitis, infantile eczema, contact dermatitis and psoriasis vulgaris.

In the curing or treatment of these inflammatory diseases, the cream of this invention can be topically applied to the lesion. The amount of the cream to be applied varies depending upon the concentration of the active ingredient of the cream. Generally, a suitable amount of it is applied to the lesion once to several times a day depending upon the severity of the disease treated.

The excellent storage stability and skin absorbability of the cream of this invention can be illustrated by the following test examples.

TEST EXAMPLE 1

Creams of varying pH values were prepared by the same procedure as in Example 1 given hereinbelow by varying the amount of the pH adjusting agent. These creams are designated as samples A, B, C, D and E. The samples were stored at 40° C. for 3 months, and the ratio (%) of residual hydrocortisone butyrate propionate was measured. The results are shown in Table 1.

TABLE 1

| Storage stability (40° C., 3 months) | | |
| --- | --- | --- |
| Sample | pH of the sample (*) | pH of the sample upon dilution with distilled water to 20 times | Ratio (%) of residual hydrocortisone butyrate propionate |
| A | 2.8 | 3.5 | 84.5 |
| B | 4.2 | 4.5 | 98.5 |
| C | 4.7 | 5.0 | 99.5 |
| D | 5.8 | 6.0 | 97.5 |
| E | 7.0 | 7.0 | 75.0 |

(*) Since the pH of the sample (cream) itself was difficult to measure directly, it was calculated from its pH measured upon dilution with distilled water to 20 times.

TEST EXAMPLE 2

Creams (samples F, G, H and I; the samples F and I are creams of the invention) in accordance with the recipes shown in Table 2 were prepared by the procedure of Example 1 given hereinbelow.

TABLE 2

| Recipes of creams (g) | | | | |
| --- | --- | --- | --- | --- |
| | Samples | | | |
| Ingredients | F | G | H | I |
| Hydrocortisone butyrate propionate | 0.1 | 0.1 | 0.1 | 0.01 |

TABLE 2-continued

| | Recipes of creams (g) | | | |
|---|---|---|---|---|
| | Samples | | | |
| Ingredients | F | G | H | I |
| Cetostearyl alcohol | 6.0 | 6.0 | — | 6.0 |
| Stearyl alcohol | — | — | 30.0 | — |
| Soft liquid paraffin | 20.0 | — | — | 20.0 |
| White Vaseline | 5.0 | — | — | 5.0 |
| Isopropyl myristate | — | 20.0 | — | — |
| Stearic acid | — | — | 5.0 | — |
| Nikkol TS10 (polyoxy-ethylene sorbitan monostearate) | 5.0 | 7.0 | — | 5.0 |
| Nikkol SS10 (sorbitan monostearate) | 3.0 | 3.0 | — | 3.0 |
| Ethyl paraben | 0.1 | 0.1 | — | 0.1 |
| Citric acid | 0.05 | 0.05 | — | 0.05 |
| Polyethylene glycol 6000 | — | — | 5.0 | — |
| Propylene glycol | 14.0 | 10.0 | balance | 14.0 |
| Purified water | balance | balance | — | balance |
| Total | 100 | 100 | 100 | 100 |
| pH of the sample (*) | 4.8 | 4.8 | 7.0 | 4.8 |
| pH of the sample upon dilution with distilled water to 20 times | 5.1 | 5.1 | 7.0 | 5.1 |

(*): Same as the footnote to Table 1.

Twenty healthy male adults were selected as subjects. About 50 mg of each of the samples F, G, H and I was coated on adhesive tapes for patch testing (made by Torii Pharmaceutical Co., Ltd.; small size), and the adhesive tapes were applied to the forearms of the individual subjects. Four hours later, the adhesive tapes were removed, and the samples remaining on the skin were well wiped off with a gauze impregnated with 70% ethanol.

The vasoconstricting reaction was examined 2 hours and 4 hours after removal of the samples, and the degree of the reaction was evaluated in four grades and expressed by average points.

++: Became exceedingly pale and white ... 3 points
+: Became clearly pale and white ... 2 points
±: Become slightly pale and white ... 1 point
—: Did not become pale and white at all ... 0 point the results are tabulated in Table 3.

TABLE 3

| | Vasoconstricting action | |
|---|---|---|
| | Time elapsed | |
| Sample | 2 hours | 4 hours |
| F | 2.4 | 2.5 |
| G | 1.7 | 1.95 |
| H | 0.7 | 1.3 |
| I | 1.95 | 2.00 |

It is clear from the results given in Table 3 that the creams of the invention (samples F and I) have improved skin absorbability of the main active ingredient relative to the comparative creams (samples G and H) prepared in accordance with a customary method. In particular, sample I shows equivalent skin absorbability to sample G in spite of the fact that the concentration of the main active ingredient of sample I is one-tenth of that sample G. These results clearly show that the absorbability of the cream of this invention through the skin is very high.

The following Examples illustrate the preparation of the cream of this invention.

EXAMPLE 1

Twenty grams of light liquid paraffin, 5 g of white Vaseline, 6 g of cetostearyl alcohol, 5 g of Nikkol TS10 (polyoxyethylene sorbitan monostearate), 3 g of Nikkol SS10 (sorbitan monostearate) and 0.1 g of ethyl paraben were dissolved at 70° C. to prepare a component A'. Then, 0.1 g of hydrocortisone butyrate propionate was dissolved in 10 g of propylene glycol at 70° C. to prepare a component B'. Citric acid (0.05 g) was dissolved in 51 g of purified water to prepare a component C'. With stirring at 70° C., the component B' was added to the component A', and the the mixture was stirred. Then, the component C' was added to form an emulsion. The emulsion was cooled with stirring to form 100 g of a cream.

When the cream was diluted with distilled water to 20 times its volume, it had a pH of 5.0.

| Example 2 | |
|---|---|
| Hydrocortisone butyrate propionate | 0.01 g |
| Liquid paraffin | 10.0 g |
| White Vaseline | 20.0 g |
| Cetyl alcohol | 5.0 g |
| Nikkol TO10 (polyoxyethylene sorbitan monooleate) | 4.0 g |
| Nikkol SS10 (sorbitan monostearate) | 2.0 g |
| Methyl paraben | 0.2 g |
| Propylene glycol | 5.0 g |
| Glycerol | 5.0 g |
| Citric acid | 0.03 g |
| Purified water | balance |
| Total | 100 g |

A cream of the above recipe was prepared by the procedure of Example 1. It had a pH of 5.5 when it was diluted with distilled water to 20 times its volume.

| Example 3 | |
|---|---|
| Hydrocortisone butyrate propionate | 0.5 g |
| Paraffin | 5.0 g |
| Liquid paraffin | 20.0 g |
| Stearyl alcohol | 10.0 g |
| Nikkol MYS25 (polyoxyethylene sorbitan monostearate) | 7.0 g |
| Nikkol SO10 (sorbitan monooleate) | 3.0 g |
| Propyl paraben | 0.1 g |
| Ethylene glycol | 15.0 g |
| Citric acid | 0.07 g |
| Purified water | balance |
| Total | 100 g |

A cream of the above recipe was prepared by the procedure of Example 1. It had a pH of 4.8 when it was diluted with distilled water to 20 times its volume.

| Example 4 | |
|---|---|
| Hydrocortisone butyrate propionate | 0.1 g |
| White Vaseline | 30.0 g |
| Stearyl alcohol | 10.0 g |
| Sodium laurylsulfate | 1.0 g |
| Nikkol MGS (glycerin monostearate) | 2.0 g |
| Propylene glycol | 10.0 g |
| Methyl paraben | 0.2 g |
| Citric acid | 0.04 g |
| Purified water | balance |
| Total | 100 g |

A cream of the above recipe was prepared by the procedure of Example 1. It had a pH of 5.2 when it was diluted with distilled water to 20 times its volume.

What we claim is:

1. An oil-in-water type cream for topical application consisting essentially of:
   (a) 0.01 to 0.5% by weight of hydrocortisone butyrate propionate,
   (b) 5 to 50% by weight of a higher paraffinic hydrocarbon component selected from the group consisting of light liquid paraffin, liquid paraffin, white petrolatum, yellow petrolatum, paraffin, ceresin and a mixture thereof,
   (c) 3 to 15% by weight of a surface-active agent component having a total HLB of 9 to 12 consisting of a member selected from the group consisting of a sorbitan fatty acid ester, a glycerin fatty acid ester, a propylene glycol fatty acid ester, and a mixture thereof, said surface-active agent component being the only surface-active agent component in the cream,
   (d) 30 to 65% by weight of purified water,
   (e) 5 to 15% by weight of a monohydric higher alcohol component selected from the group consisting of cetyl alcohol, stearyl alcohol, cetostearyl alcohol, myristyl alcohol and a mixture thereof,
   (f) 5 to 15% by weight of a member selected from the group consisting of a glycol having 2 to 6 carbon atoms and glycerol, and
   (g) a pharmaceutically acceptable acid selected from the group consisting of citric acid, lactic acid, phosphoric acid, tartaric acid, malic acid and maleic acid in an amount required to adjust the pH of the cream to a value in the range of 3.5 to 6.5 when it is diluted with distilled water to 20 times its volume.

2. The cream of claim 1 wherein the higher paraffinic hydrocarbon component has a viscosity of 10 to $10^6$ centipoises at 20° C.

3. The cream of claim 1 which contains the higher paraffinic hydrocarbon component in a concentration of 15 to 40% by weight.

4. The cream of claim 1 which contains the surface-active agent component in a concentration of 4 to 10% by weight.

5. The cream of claim 1 which contains purified water in a concentration of 40 to 55% by weight.

6. The cream of claim 1 wherein the amount of the pharmaceutically acceptable acid is one required to adjust the pH of the cream to 4.0 to 6.0 when it is diluted with distilled water to 20 times its volume.

7. The cream of claim 1 wherein the pharmaceutically acceptable acid is citric acid.

8. The cream of claim 1 wherein the amount of the pharmaceutically acceptable acid is one required to adjust the pH of the cream to 4.5 to 5.5 when it is diluted with distilled water to 20 times its volume.

9. The cream of claim 1 wherein the sorbitan fatty acid ester is a polyoxyethylene sorbitan fatty acid ester.

* * * * *